United States Patent [19]

Lundmark

[11] 4,218,334
[45] Aug. 19, 1980

[54] PHYTOSTEROL BLENDS

[75] Inventor: Larry D. Lundmark, Richfield, Minn.

[73] Assignee: Henkel Corporation, Minneapolis, Minn.

[21] Appl. No.: 584,319

[22] Filed: Jun. 6, 1975

[51] Int. Cl.$^2$ .................. B01F 17/00; B01F 17/38
[52] U.S. Cl. ............................ 252/356; 252/312; 252/351; 252/363.5; 252/545; 252/DIG. 13; 424/172
[58] Field of Search ............. 252/356, 351, 363.5

[56] References Cited

U.S. PATENT DOCUMENTS

| | | | |
|---|---|---|---|
| 2,344,671 | 3/1944 | Bertsch | 252/351 X |
| 2,684,338 | 7/1954 | McGowan et al. | 252/356 X |
| 3,821,121 | 6/1974 | Julian | 252/351 |

OTHER PUBLICATIONS

Kirk-Othmer Encyclopedia of Chemical Technology, 2nd Ed., vol. 22, p. 413.

*Primary Examiner*—Richard D. Lovering
*Attorney, Agent, or Firm*—Forrest L. Collins

[57] ABSTRACT

A blend including phytosterol together with saturated fatty acids and/or saturated fatty alcohols is disclosed.

6 Claims, No Drawings

PHYTOSTEROL BLENDS

The present invention relates to phytosterol blends and more particularly to blends including phytosterols together with fatty acids or fatty alcohols. The present invention also relates to the process of preparing such blends.

It has been found that phytosterols can be used advantageously in various emulsions. The phytosterols serve as auxiliary emulsifiers as well as modifiers of the consistency and appearance of the emulsion. The phytosterols act as high slip agents and as conditioning additives. The term "Phytosterol" as used herein will mean sterol obtained from plant sources. A difficulty encountered in such utilization of phytosterols results from the relatively high melting point of the phystosterols, usually at least 135° C., typically 136°-140° C. If the phytosterol is added directly to the emulsion, the emulsion and the phytosterol must be maintained at an elevated temperature over a prolonged mixing time in order to effect dissolution of the phytosterol. I have now discovered that the difficulty of effecting dissolution of the phytosterol can be overcome by blending the phytosterols with either free fatty acids or free fatty alcohols. The term "phytosterol blend" as used herein will mean a blend of phytosterol and either saturated free fatty acids or saturated free fatty alcohols.

The phytosterols used in the present invention typically may include stigmasterol, campesterol, sitosterol and/or brassicasterol. Generally, however, the phytosterol in the present invention will be a mixture of two or more of such phytosterols. The phytosterols are preferably present in the free form. However, in some instances, the phytosterols may be in the naturally occurring ester form.

The fatty acid of the present invention is the saturated fatty acids having even numbered chain lengths of from 12 to 18 carbon atoms. Typically, lauric acid, myristic acid, palmitic acid and stearic acid. It has been found undesirable to use the unsaturated fatty acids since separation of the phytosterol and such fatty acids will result upon storage at room temperature. Further, if the unsaturated fatty acids are used, discoloration of the mixture may result.

The saturated fatty alcohols utilized in the present invention include any of the alcohols having even numbered chain lengths of from 12 to 18 carbon atom members. Saturated fatty alcohols typically include lauryl alcohol, myristyl alcohol, cetyl alcohol and stearyl alcohol.

The blend of the present invention typically may include up to 50%, preferably from about 10 to 50 percent phytosterol and at least 50%, preferably from about 50 to 90 percent free saturated fatty acid and/or alcohol, by weight. (The term "percent, parts" and the like as used herein will refer to "percent, parts" and the like by weight unless otherwise specified.) The blend of the present invention may be used for any of a variety of purposes including preparation of cosmetic emulsions. The blend of the present invention may be prepared by heating the fatty acid or fatty alcohol and dispersing the phytosterol into the fatty acid or fatty alcohol. In order to facilitate more rapid dispersion, the phytosterol may be heated to a molten condition typically a temperature of at least about 135° to 140° C. and the phytosterol is dispersed in the melted fatty acid or fatty alcohol. The fatty acid or fatty alcohol may be at a temperature of at least about 45° C., preferably at least 60° C. In any event the temperature of the fatty acid or fatty alcohol is sufficient to melt same, but not so high as to degrade the fatty acid or fatty alcohol. The resulting mixture is then cooled to room temperature. In certain instances, the presence of the phytosterol actually reduces the melting point of the mixture below that of the fatty acid or fatty alcohol in its pure form. For example, in one instance in which the blend included 30 percent phytosterol and 70 percent stearic acid (Triple Pressed) the melting point of the mixture was 54° C. The melting point of the phytosterol was itself 138° C. The melting point of the stearic acid was about 69° C. A mixture including 50 percent phytosterol and 50 percent stearyl alcohol was found to have a melting point of approximately 60° C. and the melting point of the pure alcohol was approximately 60° C.

Preferred embodiments of the present invention include a mixture of from 10 to 30% phytosterol and from 90 to 70% stearic acid. The mixture is substantially free of glycerides since the presence of glycerides materially reduce the amount of sterol one may get into the stable blend. If any significant amount of glycerides are present, one is unable to prepare mixtures having 10% or more sterols present. Another such embodiment includes from 10 to 50% phytosterol and from 90 to 50% stearyl alcohol. Of course, various other embodiments come within the scope of the present invention.

EXAMPLE I

A blend was prepared according to the present invention by heating 70 parts of stearic acid (Triple Pressed) to a temperature of about 70° C. and dispersing 70 parts of a phytosterol mixture at about 135° C. into the melted stearic acid. The phytosterol mixture included about 56% sitosterol, 28% campesterol, 4% stigmasterol and 12% other materials. The blend was then cooled to room temperature. A cosmetic emulsion was prepared by dispersing one part triethanolamine in 94 parts of water. Five parts of the previously prepared phytosterol blend was then added. A control emulsion was likewise prepared including five parts of stearic acid, one part triethanolamine and 94 parts of water. The resulting emulsions were initially similar in appearance. However, the emulsion containing the phytosterol blend did not have a soapy characteristic whereas the control did have such an undesirable characteristic. Also, when the emulsion containing the phytosterol blend was applied to the skin, a smoother feel was noted. The two emulsions were aged for approximately one week at room temperature. The control remained a thick gel like consistency whereas the emulsion including the phytosterol blend became a flowable fluid thus overcoming the normally undesirable thickening characteristic of triethanolamine-stearate emulsions. The control was translucent and paracrystalline which is typical of triethanolamine-stearate emulsions. The phytosterol emulsion however was a white emulsion with a pearly sheen. This emulsion, when studied under a microscope, was found to include very fine particles. The phytosterol emulsion was centrifuged and it was found that the very fine particles remained in emulsion.

EXAMPLE II

A series of blends were prepared to identify the capillary melting point of stearic acid-phytosterol mixtures. The phytosterol included 56% sitosterol, 28% campesterol, 4% stigmasterol and 12% other materials. The mixtures were prepared as described in Example I. The ratios of stearic acid-phytosterol were as shown in Table I.

Table I

| Sample | A | B | C | D | E | F | G | H | I | J | K | L |
|---|---|---|---|---|---|---|---|---|---|---|---|---|
| Phytosterol (percent) | 0 | 5 | 10 | 20 | 30 | 40 | 50 | 60 | 70 | 80 | 90 | 100 |
| Stearic Acid* | 100 | 95 | 90 | 80 | 70 | 60 | 50 | 40 | 30 | 20 | 10 | 0 |
| Melting Point, °C. | 68 | 56 | 56 | 55 | 54 | 73 | 101 | 101 | 112 | 119 | 127 | 136 |

*Triple Pressed

A Eutectic mixture is noted between the stearic acid/phytosterol ratios of 5/95 to 30/70.

EXAMPLE III

Example II was repeated except that the blend was of stearyl alcohol and the phytosterol mixture. The ratios of stearyl alcohol and phytosterol was as shown in Table II.

Table II

| Sample | A | B | C | D | E | F | G | H | I | J | K | L |
|---|---|---|---|---|---|---|---|---|---|---|---|---|
| Phytosterol (percent) | 0 | 5 | 10 | 20 | 30 | 40 | 50 | 60 | 70 | 80 | 90 | 100 |
| Stearyl Alcohol | 100 | 95 | 90 | 80 | 70 | 60 | 50 | 40 | 30 | 20 | 10 | 0 |
| Melting Point, °C. | 59 | 58 | 58 | 57 | 59 | 59 | 59 | 101 | 111 | 117 | 123 | 136 |

A substantially reduced melting point is maintained through a 50:50 mixture of stearyl alcohol and phytosterol.

EXAMPLE IV

A blend including iso-stearic acid and phytosterol was prepared by heating 90 parts iso-stearic acid (Emery 875-D Isosteric Acid TM) to 80° C. and then blending in 10 parts of phytosterol. The mixture was cooled to room temperature. A stable clear liquid was obtained.

EXAMPLE V

A blend was prepared as described in Example IV except the iso-stearic acid was replaced with iso-stearyl alcohol. Similar results were obtained.

EXAMPLE VI

A shampoo was prepared incorporating the present fatty acid and phytosterol. 450 parts of iso-stearic acid were heated in a stainless steel container to a temperature of 70° C. Phytosterol in an amount of 50 parts was added with stirring. A clear solution was obtained. The solution was cooled to room temperature. A shampoo having the following composition was prepared.

Table III

|  | % | Grams |
|---|---|---|
| Sodium lauryl sulfate (30% aqueous solution) | 62.8 | 628 |
| Phytosterol - fatty acid blend | 3.3 | 33 |
| Triethanolamine lauryl sulfate (40% solution) | 4.6 | 46 |
| KOH Solution 34% | 1.0 | 10 |
| Mixture of lauric and myristic diethanolamides (Clindrol 100 LM™) | 1.5 | 15 |
| Water | 26.8 | 268 |
|  |  | 1000 |

The water was placed in a vessel and heated to 70° C. The KOH solution was added with mixing. The phytosterol fatty acid was mixed in. The sodium lauryl sulfate solution was added and the temperature was raised to 85° C. and maintained between 80° and 85° C. for about 20 minutes and then cooled to 55° C. The mixture of lauric and myristic diethanolamides was added and mixed until dissolved. The resulting mixture was cooled to room temperature and sufficient water was added to bring the final weight to 1000 grams. This was to compensate for the water that was lost. A portion (96 grams) of the resulting shampoo was placed in a beaker and 4 grams of glycerol was added. The mixture was heated to about 80° C. and stirred for five minutes. The resulting mixture was used to wash hair tresses.

EXAMPLE VII

A blend was prepared according to the present invention by heating 70 parts reagent grade lauric acid to about 45° C. and adding thereto the phytosterol mixture described in Example I. The phytosterol mixture was at 135° C. The blend was stirred until it became viscous and then allowed to remain undisturbed until solidification took place. The melting point of the blend was found to be about 50° C.

EXAMPLE VIII

A blend was prepared as described in Example VII except the reagent grade lauric acid was replaced with cosmetic grade lauric acid (Neo-Fat 12 TM produced by Armak). The results were similar except the melting point of the blend was found to be about 56° C.

EXAMPLE IX

A blend was prepared by adding 7 parts reagent grade myristic acid and 3 parts of the previously described phytosterol mixture to a beaker. The beaker was heated until the ingredients melted. The blend was allowed to cool with stirring until it became viscous. The blend then remained undisturbed until it solidified. The blend had a melting point of about 57° C.

EXAMPLE X

Example IX was repeated using palmitic acid. The blend had a melting point of about 67° C.

EXAMPLE XI

A blend was prepared according to the present invention by placing 7 parts dodecyl alcohol and 3 parts phytosterol (primarily sitosterol) in a beaker and heating until the materials melted. The blend was then cooled with stirring until it became viscous. It was then allowed to solidify. The resulting blend had a melting point of about 30° C.

EXAMPLE XII

Example XI was repeated, however, using cetyl alcohol. The resulting blend had a melting point of about 50° C.

EXAMPLE XIII

Example XI was repeated using instead myristyl alcohol. The resulting blend had a melting point of about 62° C.

EXAMPLE XIV

A comparison was made of the ease of incorporating the present blend into mineral oil in relation to the ease of incorporating the separate ingredients. A blend was prepared including 23 grams stearic acid and 10 grams phytosterol. The phytosterol was a mixture including 56% sitosterol, 28% campesterol and 4% stigmasterol (sold by General Mills Chemicals, Inc. under the trademark Generol 122). The stearic acid and phytosterol were placed in a beaker and heated to 110° C. with mixing until they were clear. The mixture was cooled to 80° C. and poured in a thin layer onto a sheet of aluminum foil to cool. After reaching room temperature, the blend was broken up into flakes. Sixty seven grams of mineral oil were placed in each of two beakers (A and B). Beakers A and B containing the mineral oil were then each heated to and held at 80° C. Thirty three grams of the blend were added to the mineral oil in beaker A with constant agitation until the solution became clear which required 40 seconds. Ten grams of the phytosterol and 23 grams of the stearic acid were added to the mineral oil in beaker B with constant agitation until the solution became clear. This required 240 seconds. The use of the present blend was found to have substantial advantage over addition of the separate materials.

EXAMPLE XV

Example XIV was repeated except the stearic acid was replaced with stearyl alcohol. The blend dissolved in the mineral oil in 50 seconds; whereas the separate stearyl alcohol and phytosterol alcohol required 180 seconds to form the clear solution.

The embodiments of the invention in which an exclusive property or privilege is claimed are defined as follows:

1. A blend consisting essentially of from about 10 to 50 percent phytosterol and from about 50 to 90 percent of a member of the group consisting of free saturated fatty acids and free saturated fatty alcohols having an even number of carbon atoms from 12 to 18 in number, said blend being substantially free of triglyceride.

2. The blend of claim 1 wherein said member is a free saturated fatty acid.

3. The blend of claim 2 wherein said free fatty acid is stearic acid and said blend has between 10 and 30% phytosterol and between 90 and 70% stearic acid.

4. The blend of claim 2 wherein the fatty acid is lauric acid.

5. The blend of claim 2 wherein the fatty acid is myristic acid.

6. The blend of claim 2 wherein the fatty acid is palmitic acid.

* * * * *